United States Patent
Kip et al.

[11] Patent Number: 5,952,660
[45] Date of Patent: Sep. 14, 1999

[54] METHOD OF IDENTIFYING POST CONSUMER OR POST INDUSTRIAL WASTE CARPET UTILIZING A HAND-HELD INFRARED SPECTROMETER

[75] Inventors: Berend J. Kip, Sittard; Edo A. T. Peters, Maasrtricht, both of Netherlands; Jens Happel, Münster, Germany; Thomas Huth-Fehre, Münster, Germany; Frank Kowol, Münster, Germany

[73] Assignees: DSM N.V. & Institut fur Chemo, Heerlen, Netherlands; Biosensorik, Munster, Germany

[21] Appl. No.: 09/003,502

[22] Filed: Jan. 6, 1998

Related U.S. Application Data

[63] Continuation of application No. PCT/NL96/00280, Jul. 5, 1996.

[30] Foreign Application Priority Data

Jul. 6, 1995 [NL] Netherlands ............................ 1000738

[51] Int. Cl.$^6$ .............................. G01J 3/42; G01N 21/35; G01N 21/25
[52] U.S. Cl. .................................. 250/339.11; 250/341.8; 250/339.01; 250/339.02; 250/339.07
[58] Field of Search .......................... 250/339.01, 339.02, 250/339.07, 339.08, 339.09, 339.11, 339.12, 341.1, 341.8

[56] References Cited

U.S. PATENT DOCUMENTS

| | | |
|---|---|---|
| 2,823,577 | 2/1958 | Machler . |
| 3,696,247 | 10/1972 | McIntosh et al. . |
| 3,880,523 | 4/1975 | Thomas et al. . |
| 4,043,668 | 8/1977 | Goetz et al. . |
| 4,560,275 | 12/1985 | Goetz et al. . |
| 4,975,581 | 12/1990 | Robinson et al. ................. 250/339.09 |
| 5,822,219 | 10/1998 | Chen et al. .............................. 364/498 |

OTHER PUBLICATIONS

S. Ghosh et al., Schnelle Indentifizierung von Hitzefixierten Teppichgamen durch Reflexionsanalyse in nahen Infrarotgebiet, Melliand Textilberichte, 1988, vol. 5 pp. 361–364.

H.E. Korth, Spectrophotometric film and color analyzer, IBM Technical Disclosure Bulletin, Feb. 1984, pp. 4811–4812.

Nishigaki Hidehisa, Shimadzu Corp., Spectrophotometer, Patent Abstracts of Japan, Oct. 1986, pp 507, Pub. No.–JP61120023.

*Primary Examiner*—Constantine Hannaher
*Assistant Examiner*—Albert Gagliardi
*Attorney, Agent, or Firm*—Pillsbury Madison & Sutro, LLP

[57] ABSTRACT

A method and apparatus for use in the recycling of post consumer or post industrial waste carpet or Polyamide-6 and/or Polyamide-66 containing non-carpet waste utilizes a hand-held portable device utilizing spectroscopic principles to accurately and quickly identify the material of the waste (carpet). The spectrometer envisioned for this task includes an infrared radiation source for illuminating the waste (carpet) sample, a selector for selecting a predetermined number of discrete wavelengths and a detection system to detect reflected radiation within the discrete wavelengths. The selector can be either a plate with a plurality of slots which positionally correspond to locations in a dispersed light beam according to the predetermined discrete wavelengths or a plurality of filters selected to pass the discrete wavelengths. The selection of the discrete wavelengths can either take place before the carpet sample is irradiated or can take place by selecting the discrete wavelengths from reflected radiation.

24 Claims, 4 Drawing Sheets

METHOD OF IDENTIFYING POST CONSUMER OR POST INDUSTRIAL WASTE CARPET UTILIZING A HAND-HELD INFRARED SPECTROMETER

This is a continuation of International Appln. No. PCT/NL96/00280 filed Jul. 5, 1996.

BACKGROUND OF THE INVENTION

1. Field of the Invention

The invention relates to a method and apparatus for identifying post consumer or post industrial waste carpet using an infrared (IR) spectrometer, and more particularly to a method of identifying post consumer or post industrial waste carpet using a hand-held IR spectrometer having an IR radiation source which illuminates the post consumer or post industrial waste carpet with IR radiation, a selector for selecting a predetermined number of discrete wavelengths of radiation and an IR detection system for detecting radiation reflected by the post consumer or post industrial waste carpet. The invention also relates to a method and apparatus for identifying Polyamide-6 and/or Polyamide-66 containing material using a hand-held IR-spectrometer enabling sorting of the Polyamides.

2. Description of the Related Art

Recycling post consumer or post industrial waste carpet material requires the post consumer or post industrial waste carpet material to be sorted according to the type of face fiber used to manufacture the carpet. Throughout this application, applicants will repeatedly refer to "post consumer waste carpet", which is used by applicants as a generic term encompassing both post consumer waste carpet, post industrial waste carpet and Polyamide-6 and/or Polyamide-66 containing waste streams.

Currently, carpets employ face fibers produced from materials such as Polyamide-6, Polyamide-66, Polypropylene, Wool, Polyester and blends of these component products. For a recycling program to be successful, it must be easy to accurately identify the type of face fiber used by the carpet.

One method of identifying carpets is to print a code on the back of the carpet. Unfortunately, although this is the most fool-proof of all possible methods, it requires the carpets to have been marked when manufactured. Therefore, even if marking was started today, this method would not become effective for approximately 10 years due to the expected life of the marked carpet. Further, this method may not be satisfactory when used with glued carpets, since the backing of glued carpets may be damaged, thus rendering the identification code difficult to read.

Alternatively, it is possible to identify the type of carpet by detecting the melting point of the face fiber. This identification method is inadequate because it is not able to separate streams of Polyester and Polyamide-66. Further, blends of the various types of face fibers cannot be distinguished. Devices which utilize the melting point of the carpet material as a distinguishing characteristic are also deficient in that they generally tend to have a long warm-up time, thus reducing efficiency, and can be dangerous since they necessarily involve hot components.

A third way to identify the type of face material used on a particular waste carpet sample is to use a spectroscope. It is well known that various materials can be identified using vibrational spectroscopic techniques like mid-infrared and near infrared spectroscopy. In particular, near infrared spectroscopy is a well known method, e.g. for the sorting of bottles. IR spectroscopy can be conducted on transparent materials by analyzing radiation passing through the materials, and on substances which are opaque to IR radiation by analyzing the diffuse radiation reflected by the material. To conform with the customary usage in optics, this application will sometimes refer to IR radiation as "light".

IR spectrometers, for both the near-infrared range (800–2500 mm) and the mid-infrared range (2500–25000 mm), are often used to identify and quantify materials on the basis of the material characteristics which cause them to absorb or reflect particular wavelengths. In many cases, these characteristic frequencies are only slightly different for different materials. It is therefore important to use a high spectral resolution spectrometer, especially when attempting to distinguish various materials mixed together.

An IR spectrometer generally includes a source which emits radiation in the desired wavelength range and auxiliary optics such as lenses and mirrors to form the radiation into a beam of suitable shape and dimensions and to guide it along a light path. As a rule, all elements that make up the spectrometer are accommodated in an enclosure which preferably is sealed to prevent dust from interfering with the components.

The light source is preferably placed in a reflector casing so that the spectrometer can obtain as much light as possible. The light source is preferably incorporated in the optical casing, so that light egresses from the spectrometer via an optically transparent window to impinge on the target material. The transparent window may be, for instance, glass or high-quality quartz or may be made of for instance KBr, KCl, ZnSe, $KRS_5$, $CaF_2$ or $MgF_2$ for the mid-infrared range.

The beam is directed at a site on the material to be examined. The reflected radiation is then collected, formed to have a desired beam geometry and eventually directed onto a detection system. This detection system normally includes a detector capable of measuring the intensity of the incident radiation. Several detectors which may be used in the near-infrared range include PbS and InGaAs detectors, and detectors which may be used in the mid-infrared range include detectors made from deuterized triglycinesulphate (DTGS).

There are several basic types of IR spectrometers. Two types of IR spectrometers are discussed below. In the first type, discrete wavelengths are selected by passing reflected radiation through different filters that are only transparent to a particular wavelength range. In the second type, a beam of reflected IR radiation is dispersed and allowed to impinge on a diode array. Unfortunately, diode arrays of this nature and having the desired resolving power are very expensive, and selection of the desired wavelength from the absorbed spectrum must take place in a later phase in the downstream processing equipment, thus increasing the amount of support electronics necessary to utilize the spectrometer.

The relationship between the intensity and the wavelength of the reflected or transmitted light from a particular material is called the spectrum. The detector is linked to a processing system which converts the detector signals into a spectral form accessible to the user or a computer such as a curve or numerical values.

In general, the mid- and near-infrared spectra of various types of fibers used in carpets differ significantly. However, the spectra of polyamide-6 and polyamide-66 differ only slightly: the mid-infrared spectrum is completely identical and the near infrared spectra is only slightly different in the 2000–2500 nm spectral range.

The quality of identification obtainable using a given spectroscopic system is expressed as the Mahalonobis-distance (MD), which is the center-to-center distance between the various clusters in relation to the spread within the clusters. For good separation, a minimum MD value of about 6 is required, but ideally the value should be larger than 10.

Unfortunately, although Ghosh and Rogers (Melliand Textilberichte 5, 1988, pages 361–364) indicated that the scanning spectrometer in their system achieved very good MD results for sorting Polyamide-6 and Polyamide-66 fibers (MD=18), the size and price of the scanning spectrometer renders this system largely unsuitable for use in the carpet recycling business. Ghosh and Roogers also demonstrated that it is possible to identify nylon 6 and nylon 66 fibers used for carpet production using a Bran&Luebbe (Formerly Technicon) InfraAlyzer 500C, with a combination of 3 filters, (2250, 2270 and 2310 nm).

These reported results are also deceiving, in that used carpets have different fiber materials than new carpets due to wear and contamination, thus complicating identification. For example, using these same 3 filters on a sample of 113 post consumer carpet waste samples, applicants discovered that the obtainable MD ranged between 4, and 1.2, depending on the resolution of the spectrometer. As indicated above, results of this nature are clearly insufficient to accurately discriminate between various carpet samples. Accordingly, it still has not been demonstrated to be possible to distinguish various types of post consumer waste carpet utilizing a cheap, small and portable spectrometer based on selected wavelengths.

Likewise, although portable inexpensive IR filter-based spectrometers are commercially available for task specific applications, such as to determine the moisture content of various materials, no one has been able to develop a hand-held spectrometer which is able to satisfactorily distinguish between various types of carpet face material so that the spectrometer can be suitably used in recycling post consumer waste carpet.

SUMMARY OF THE INVENTION

One object of the invention is to provide a method of reliably analyzing post consumer carpet waste using a hand-held IR spectrometer. To do this, the invention utilizes a hand-held spectrometer which is capable of measuring at a number of discrete wavelengths with sufficient resolution.

Two such hand-held spectrometers are envisioned in this respect. The first hand-held spectrometer is capable of measuring a number of discrete wavelengths with good resolution by utilizing a radiation selector which disperses the radiation and selects discrete wavelengths from the dispersed radiation using a plate provided with openings at locations corresponding to the positions of the discrete wavelengths in the dispersed radiation to be selected.

The second hand-held spectrometer is also capable of measuring a number of discrete wavelengths, but utilizes filters which pass particular selected wavelengths optimal for use in the carpet recycling business.

Depending on the application to which the spectrometer will be applied, the spectra in the near-infrared range or the mid-infrared range of a series of samples are recorded using a high-resolution spectrometer. These high-resolution spectra are used to determine the combination of absorptions at different wavelengths which yield sufficient information for discriminating one polymer from another. In the case of carpet recycling, for instance, one might wish to know if a carpet is made of Polypropylene, Polyamide-6, Polyamide-66 or Polyethylene Terephthalate (PET).

Absorption of the detector should be checked against a reference material of a known substance. Suitable reference materials for diffuse reflection in the near-infrared range include, for example, small ceramic plates and small teflon plates.

Absorption is calculated as follows:

$$A_\lambda = \log (I_{\lambda(sample)}/I_{\lambda(reference\ material)}), \tag{1}$$

where $A_\lambda$ is the absorption at wavelength $\lambda$ and $I_\lambda$ is the light intensity at wavelength $\lambda$. An analysis is obtained on the basis of the absorption at different wavelengths using standard mathematical methods. The analyses may be used for identifying and/or quantifying samples with the aid of chemometric methods. Chemometric methods for identification are described, for example, in Ghosh et al, Melliand Textilberichte 5 (1988) 361.

In order to be able to identify samples of various types of carpets, a mathematical analysis is made to establish the combination of wavelengths which ensures the best separation between the different materials to be identified. For a series of used and unused carpets, spectra can be recorded in the near-infrared range with a resolution of 2 nm. The separation is calculated using cluster analysis for all possible combinations of, for example, 3 wavelengths ($\lambda 1$, $\lambda 2$, $\lambda 3$).

To do this, the values of, for example, $A(\lambda 2)-A(\lambda 1)$ and $A(\lambda 3)-A(\lambda 2)$ are calculated, where $A_\lambda$ is the absorption at the wavelengths specified. When these values are plotted on a graph, there appear to be separate clusters for the different materials at different wavelength combinations. The quality of separation increases accordingly as the clusters are better isolated from one another. Optimum separation is accomplished by selecting the combination of, for instance, 3 wavelengths at which the Mahalanobis' distances between the 3 clusters (4 different Mahalanobis' distances) are maximum.

To separate Polyamide-6, Polyamide-66, PET and polypropylene, a combination of the absorptions at 2432, 2452 and 2478 appears to be optimum. In this way, it is possible to determine which discrete wavelengths should be measured for a particular application to clearly distinguish the different materials with the spectrometer of this invention. Then, using standard optical calculation methods, the locations of the holes in the plate can be easily determined depending on the particular combination of grating, entry slit, grating-to-plate distance, etc.

A more extensive and broad optimization is done mathematically using a technique called 'genetic algorithms'. In this technique, the full spectrum of various samples are taken using a high quality scanning spectrometer having good spectral resolution and signal/noise ratios. The set of spectra are transformed to simulate spectral resolutions that are worse (e.g. 10 nm, 20 nm, 30 nm and 40 nm) since for cheap hand-held devices the resolution is less than for research-grade spectrometers. In addition, the signal/noise ratio and the accuracy of the wavelength selection is less for hand-held devices. These effects must therefore also be included in the wavelength selection procedure.

In the genetic algorithms optimization procedure, the optimization conditions can be defined in any desired way. For example, the optimization conditions could be set to maximize the MD of Polyamide-6 and Polyamide-66, maximize the minimum of the MD's of Polyamide-6 to the other types of materials, maximize all the MD's, etc.

An experiment was conducted using the genetic algorithms technique. In the first example, it was chosen to maximize the minimum of the MDs of Polyamide-6 to the other types of materials (Polyamide-6 Polyamide-66, Polyamide-6—Polypropylene, Polyamide-6—PET). The allowed shifts of the selected wavelengths was set to be ±6 nm, the spectral resolution was chosen at 16 nm, the signal to noise ratio was set at 200.

Four wavelengths were chosen using these parameters: 2382, 2430, 2452, 2472, which rendered the following results:

MD Polyamide-6—Polyamide-66:8.2–11.8
MD Polyamide-6—PET:16.5–22.5
MD Polyamide-6—Polypropylene:8.2–11.9

Below the IR spectrometers according to the invention are described.

The first type of IR spectrometer of this invention has been demonstrated to be capable of selecting narrower wavelength ranges than known spectrometers by dispersing incoming radiation. Dispersion in this context, means the spatial distribution of the different wavelengths which occur in a beam of radiation. One well known device useful to cause dispersion of an incoming beam of radiation is a grating. In this first spectrometer, a grating is preferably stationary and has between 100–4000 lines/mm. The reflected or transmitted light converges, with or without the aid of a system of lenses, so that it enters the grating through an inlet aperture measuring between 100 and 1000 $\mu$m.

At any distance behind the aperture, a point in the plane perpendicular to the direction of radiation corresponds with a particular wavelength. This being so, a given, desired wavelength, can be selected from the spectrum by transmitting or collecting a portion of the spectrum radiation which passes through the corresponding location.

The grating may be placed in the optical system such that the beam is reflected by the post consumer waste material. The reflected radiation may be collected, for example, in a number of suitably positioned detectors. A problem here is the minimum dimension of the available detectors, which enables adjacent wavelengths to be observed by the detector as well as the desired wavelength.

In a preferred embodiment of the IR spectrometer of this invention, this problem is resolved by selecting a discrete wavelength with a plate that is opaque to IR radiation, positioned between the source and the detection system, so that no radiation can reach the detection system other than through openings in the plate. The plate is provided with openings at locations corresponding to the positions of the discrete wavelengths in the dispersed radiation to be selected.

The openings in the plate may be made very small, in any case substantially smaller than minimum dimensions of available detectors. The openings in the plate may also be positioned with very high accuracy. In this way it is possible to accurately select the desired wavelengths from the dispersed beam of radiation with high resolution.

In this embodiment the intensities of the different wavelengths may be measured individually by placing a detector behind each opening in the plate or by using a plate and detector which are moveable relative to each other so that the detector can be serially placed behind each opening in the plate. In this case, problems associated with a finite detector dimension do not arise because the location and size of the openings independently determine the wavelength selection and resolution of the spectrometer.

Another possibility, which affords greater design flexibility, is to connect a light conductor to each of the openings in the plate and to convey the radiation to the detection system through these conductors. In this case, separate detectors may again be used, or the individual light conductors may also be connected to, for instance, a rotary system or a slide system, whereby the individual conductors may be individually disposed in front of a single detector. Alternatively, the detector may be moveable so that it can be placed in front of various stationary light conductors.

Motion of the detector or of the sliding or rotary system is preferably controlled by a computer system which also is capable of processing the measurement results. The results can, for instance, be presented on-line on a display. In this way, in a separation system for material flow, an operator can intervene on the basis of the value shown. Also, the computer can be connected to and control a downstream mechanical system. The measurement results may also be used for controlling a production process.

In another embodiment, the grating may be placed in the optical system before the radiation beam impinges on the test material. In this instance, dispersed light is passed through a plate with slots and thus selected light with the desired wavelengths is passed via light conductors onto the material. The amount of reflected light is then measured to obtain light which may be analyzed to determine the type of material.

In this case, each opening of the plate allows light of a desired wavelengths to pass. The passed light is transmitted by a light conductor, having one end positioned adjacent the slot in the plate and the other end positioned so that the exiting radiation can be aimed at the material.

Aiming the exiting radiation can be accomplished, for example, by terminating the ends of the light conductors in a rotary system which, when rotating, allows a particular light conductor to irradiate the material while optically isolating the other conductors from the material. By causing the rotary system to successively assume a number of different positions, for example, by using a stepping motor, the material can successively be irradiated with different wavelengths and the intensity of the wavelengths can be individually measured. A system of lenses may be optionally provided to ensure that the material to be examined is adequately illuminated.

Suitable light conductors for use in this system are optical fibers which are transparent to the infrared range between 1000–2000 nm. Quality glass fibers with a low SiOH content are suitable for the infrared range between 2000–2500 nm. Chalcogenide or Ag-halide fibers are suitable for the mid-infrared range. Other optical fibers that are transparent in the desired wavelength ranges may also be used. The diameter of these fibers is preferably between 100 and 1000 $\mu$m.

The positions of the openings are calculated from the desired wavelengths, the geometry of the spectrometer and the characteristics of the grating. The desired wavelengths depend on the materials to be detected and separated which determine the location of the holes in the plate. The positions of the holes can be determined using cluster analysis, as described above.

The second type of IR spectrometer of this invention uses a combination of filters placed on a filter wheel which is driven at a high speed (10–200 Hz). Using this embodiment, the sample is illuminated using a set of lamps and diffuse reflected light is collected using a lens. The light is then directed through the filter wheel and detected using a PbS or InGaAs detector.

Using a filter wheel has several unique advantages. For example, since the filter wheel blocks the light beam four times during each rotation, the dark current of the detector may be frequently sampled and used to correct for temperature drift and other fluctuations of the detector.

The collection angle for this system should be kept small, preferably less than 5°, to keep the spectral resolution of the filter below 20 nm. The detector signals are processed using an on-board microprocessor.

Alternatively, the filters can be used to select predetermined wavelengths from a source of infrared radiation before the radiation impinges on the sample of post consumer waste carpet. In this system, a filter wheel is rotated to allow infrared radiation having a predetermined wavelength range to exit of the spectrometer. The emitted light is reflected by the sample of post consumer waste carpet, and then detected by the detector.

Instead of using a filter wheel, it may also be possible to use acoustic optical tunable filters (AOTF). AOTF devices are based on acousto-optic effects in which the optical refractive index of a medium is altered using ultrasound (see *Laser Focus World,* May, 1992). Essentially, AOTF devices are crystals which receive a light beam and transmit selected wavelengths of the incident light beam based on a frequency of an acoustical input signal. Using an AOTF device, wavelengths could be selected by adjusting a frequency of ultrasound applied to the AOTF device, thus eliminating moving parts associated with a filter wheel.

BRIEF DESCRIPTION OF THE DRAWINGS

The preferred embodiments of the present invention will now be described more specifically with reference to the attached drawings, wherein.

DETAILED DESCRIPTION OF THE PREFERRED EMBODIMENTS

Figure 1:
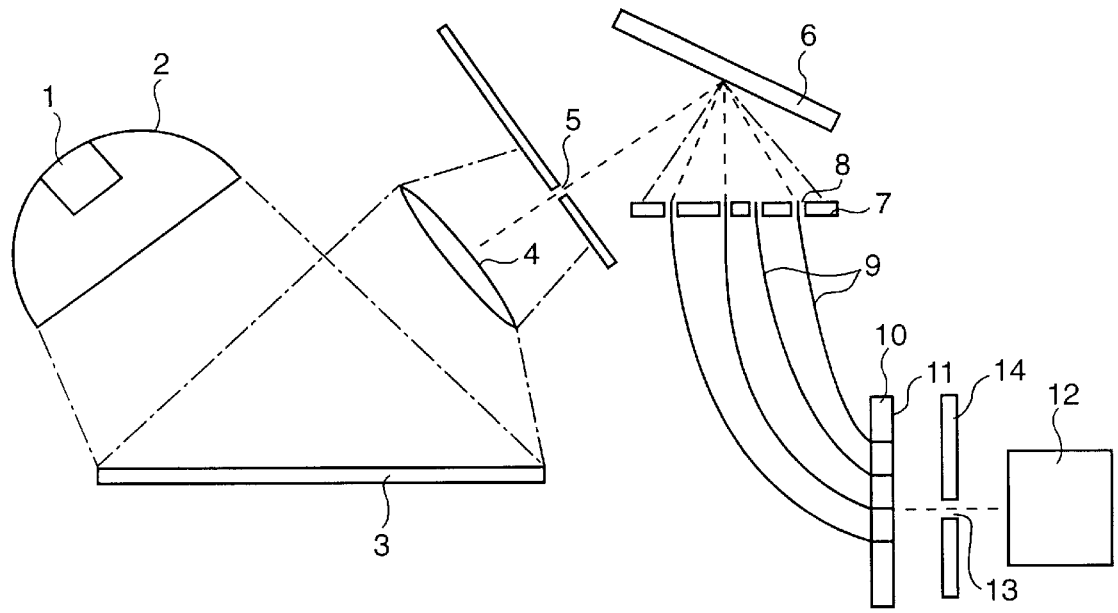
FIG. 1 is a side view of a hand-held spectrometer according to a first embodiment of this invention.

The boundaries of the radiation beams are shown in the Figs. by dot-dash lines, and individual light rays are indicated by dotted lines. In FIG. 1, a light source 1 is placed in a reflector casing 2. Light emitted from the light source 1 is directed onto a material to be examined 3. Reflected radiation converges at a lens 4, whereupon the central beam impinges on a grating 6 through an entrance slit 5. The radiation is dispersed by the grating 6 into different wavelengths. A plate 7 is placed in the dispersed radiation beam, and has openings 8 which correspond to selected wavelength positions within the spectrum. First ends of light conductors 9 are installed in the openings 8 in plate 7. The other ends of the light conductors are each inserted into an opening in selector plate 10, with the light conductors ending at a surface 11 of the plate. The selector plate 10 can be moved with a stepping motor (not shown) so that the detector 12 only sees the light from a particular light conductor through an opening 13 in an opaque plate 14 inserted between the selector plate 10 and the detector 12. The detector 12 is connected to a processing system (not shown).

Figure 2:
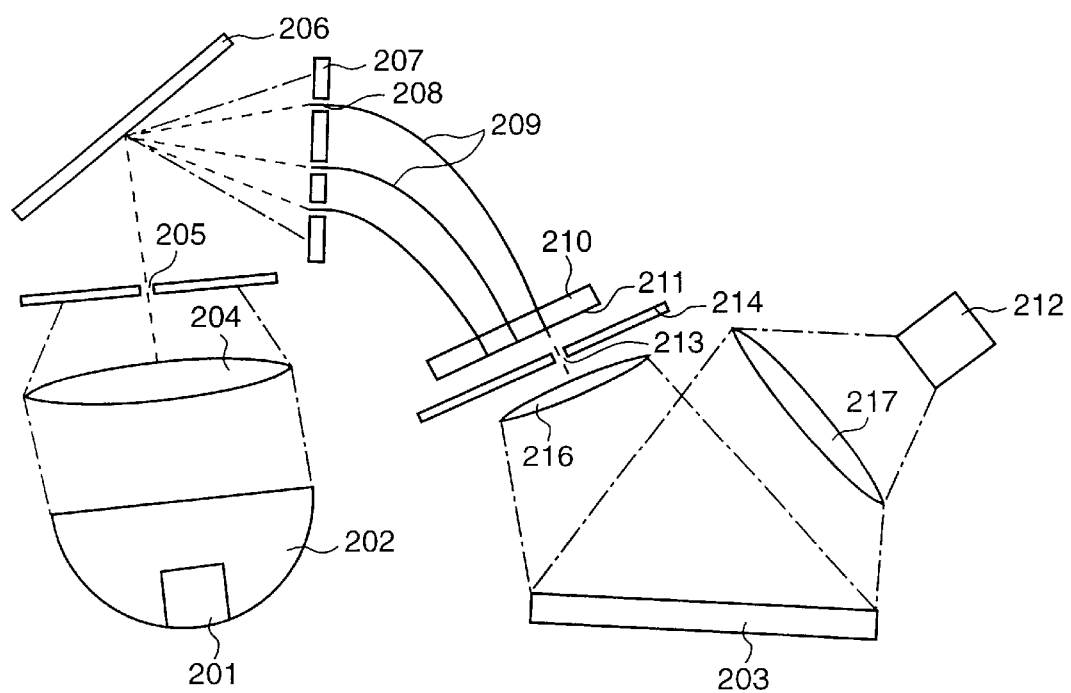
FIG. 2 is a side view of a hand-held spectrometer according to a second embodiment of this invention.

In FIG. 2, a light source 201 is placed in a reflector casing 202. The light converges at a lens 204 so that it impinges on a grating 206 through an entrance slit 205. The radiation is dispersed by the grating into different wavelengths. A plate 207 is placed in the dispersed radiation beam, which plate is provided with openings 208 positionally corresponding to selected wavelengths. First ends of light conductors 209 are installed in the openings 208 of plate 207. The other ends of the light conductors are each inserted into selector plate 210, with the light conductors ending at the surface 211 of the plate 210. An opaque plate 214 is provided behind this selector plate with an opening 213. This plate 214 can be moved with a stepping motor (not shown) so that only the light from a particular light conductor can pass through the opening 213. The light passing through this opening 213 diverges at a lens 216 whereupon the diverged radiation impinges on the material to be examined 203. The radiation reflected by the material converges at lens 217 and then impinges on detector 212. The detector is connected to a processing system (not shown).

The IR spectrometer of the invention can be made very compact for easy handling. The IR spectrometer may be advantageously used in the field recycling of plastic materials in general, provided that the specific wavelengths are selected as appropriate for the given material characteristics.

Figure 3:
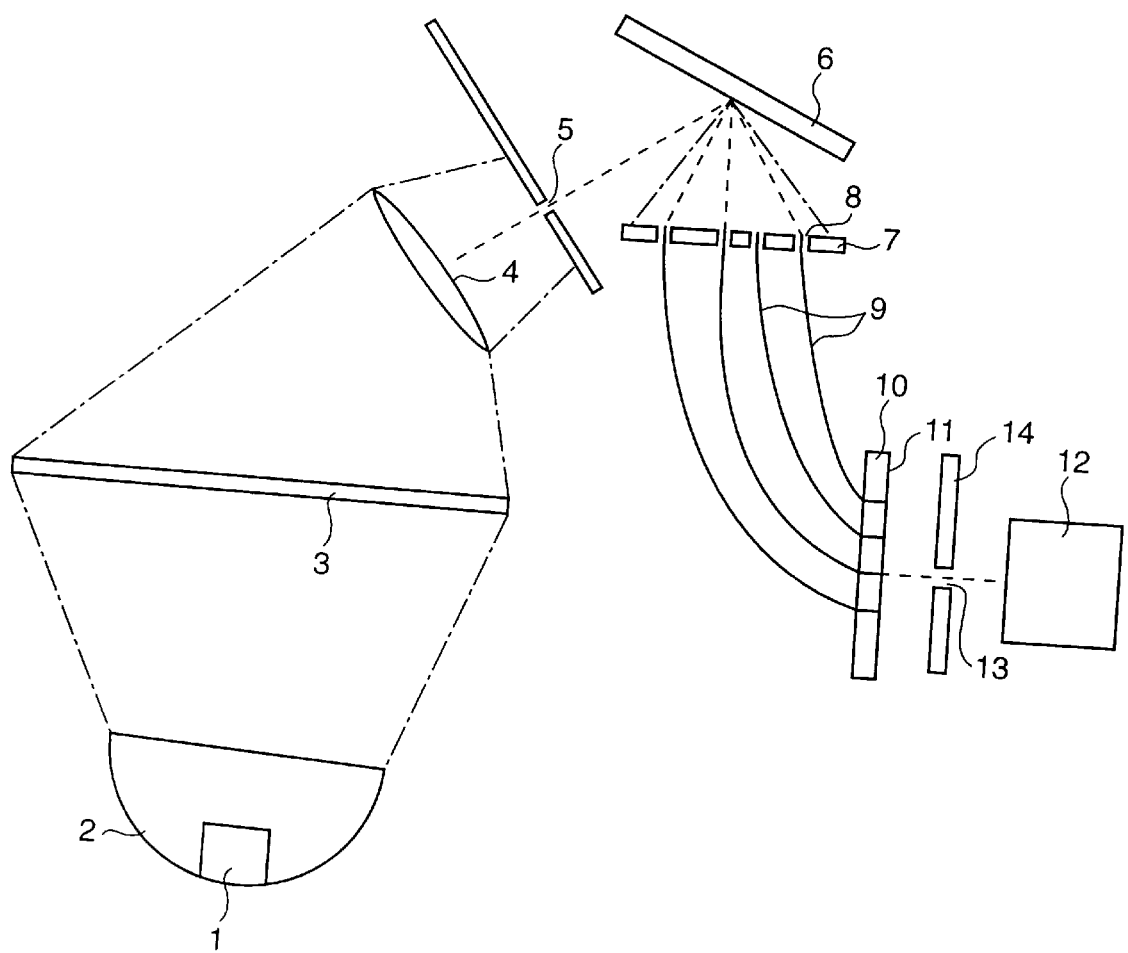
FIG. 3 is a side view of a hand-held spectrometer according to a third embodiment of this invention.
Figure 4:
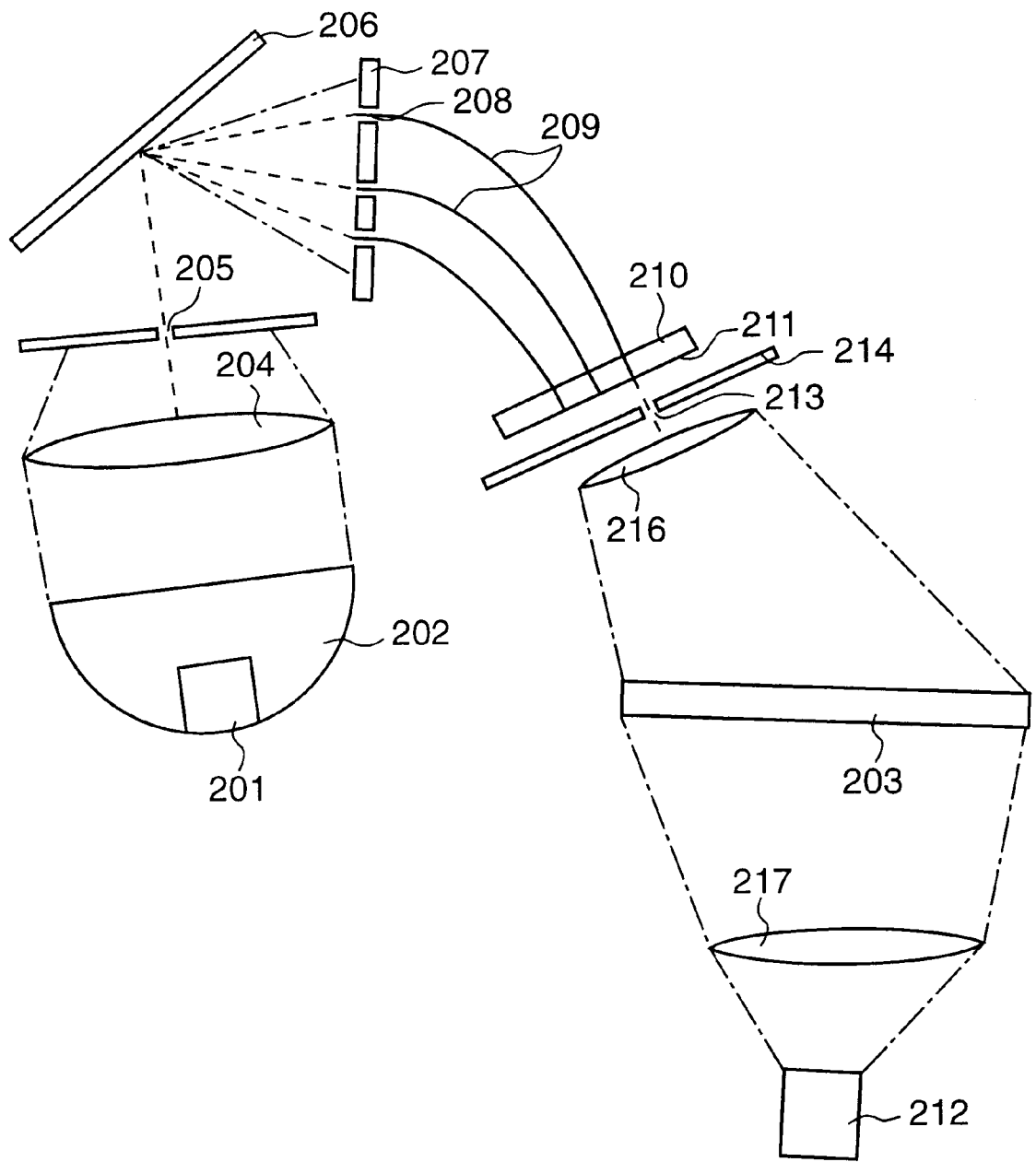
FIG. 4 is a side view of a hand-held spectrometer according to a fourth embodiment of this invention.

FIGS. 3 and 4 are identical to FIGS. 1 and 2, respectively, except that they illustrate the situation where light passing through the sample material is collected and evaluated in the spectrometer.

Figure 5:
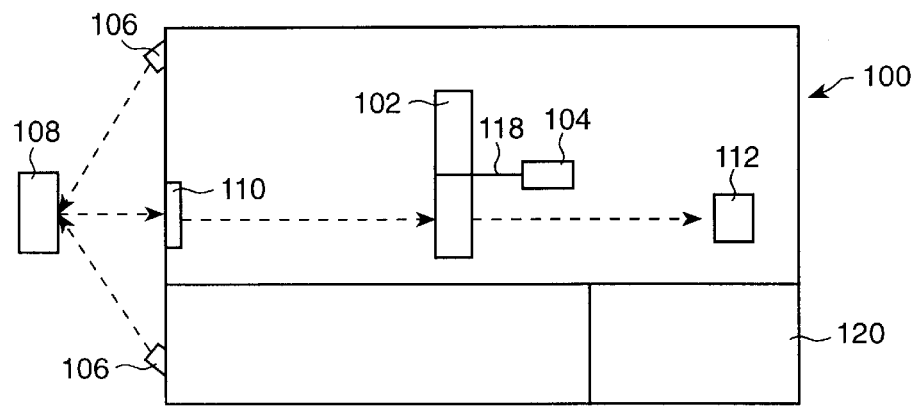
FIG. 5 is a side view of a hand-held spectrometer according to a fifth embodiment of this invention.

FIG. 5 shows a second embodiment of a device which may be used for determining the spectral qualities of post consumer waste carpet. In FIG. 5, a spectrometer 100 has a rotary filter wheel 102 which is driven by a motor 104.

Light is provided by one or more lamps 106 on one side of the spectrometer 100 to impinge on a sample of post consumer waste carpet 108. Light reflected by the sample 108 is collected by a lens 110, is directed through the rotary filter wheel 102 and sensed by a PbS or InGaAs detector 112.

Figure 6:
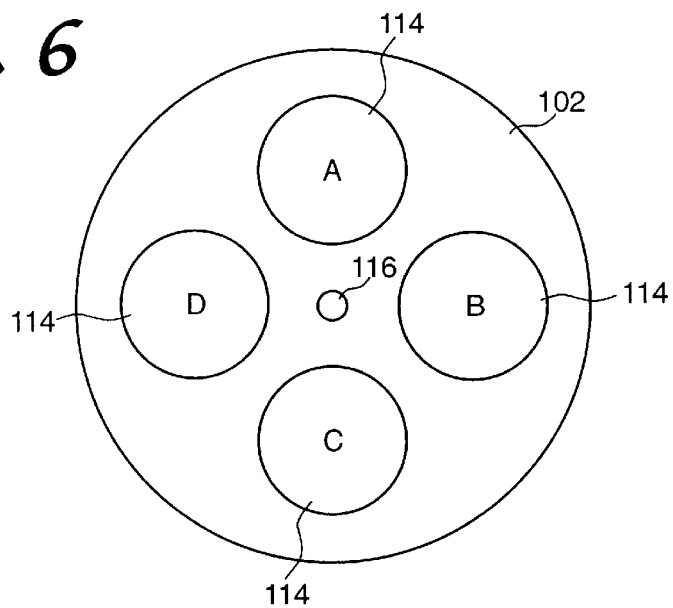
FIG. 6 is a filter wheel for use with the hand-held spectrometer illustrated in FIG. 5.

One example of a rotary filter wheel 102 is shown in FIG. 6. In this example, 4 filters 114 (A–D) are provided on the rotary filter wheel 102. A hole 116 is provided in the center of the rotary filter wheel 102 to receive a drive shaft 118 extending from the motor 104.

In operation, the motor 104 causes the rotary filter wheel 102 to rotate so that light passing through lens 110 will be filtered according to the specific qualities possessed by the filters 114. The detector 112 detects the filtered light and provides signals to an electronic circuit 120 which outputs the result.

Figure 7:
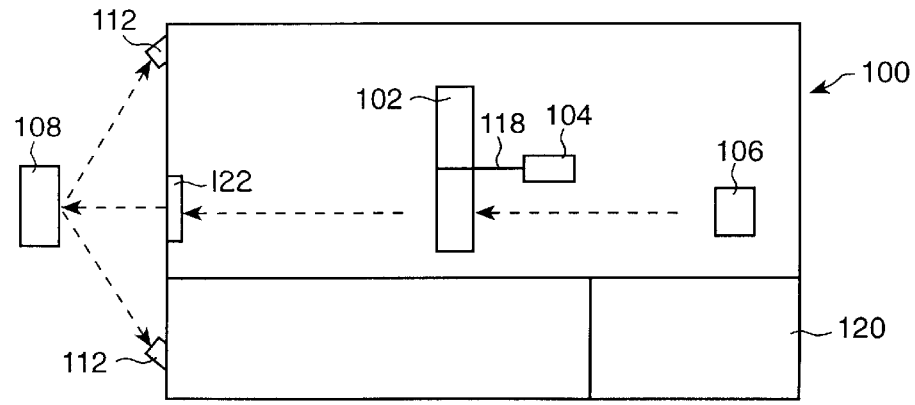
FIG. 7 is a side view of a hand-held spectrometer according to a sixth embodiment of this invention.

FIG. 7 is another example of a spectrometer 100 which utilizes a rotary filter wheel 102, except that the light is filtered before being incident on the sample of post consumer waste carpet 108. As shown in FIG. 7, a light source 106 produces infrared radiation which is filtered by a rotary filter system 102, 104, 118. The filter passes predetermined wavelengths which exit the spectrometer housing via optics 122.

After exiting the spectrometer housing, the predetermined wavelengths impinge on the sample of post consumer waste carpet 108 and are reflected by the sample of post consumer waste carpet 108. One or more detectors 112 detect the reflected light and output a signal to an electronic circuit 120 which outputs the result. Although this example has illustrated optics which emit light from only one side of the spectrometer, the light passing through the filter could alternatively be divided and exit the spectrometer at various locations.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

We claim:

1. A hand-held infrared spectrometer for use in analyzing post consumer or post industrial waste carpet or Polyamide-6 and/or Polyamide-66 containing non-carpet waste, comprising:
    an infrared radiation source for illuminating the waste (carpet) with infrared radiation;
    a selector for selecting a number of discrete wavelengths from infrared radiation reflected by the waste (carpet) in order to get a Mahalanobis-distance of at least 6; and
    an infrared detection system for detecting the selected discrete wavelengths.

2. A hand-held infrared spectrometer according to claim 1, wherein the selector comprises a dispersing device which disperses the radiation and a discrete wavelength selector which selects the discrete wavelengths from the dispersed radiation.

3. A hand-held infrared spectrometer according to claim 1, wherein the selector comprises a filter system having a plurality of filters for transmitting only predetermined wavelengths of radiation.

4. A hand-held infrared spectrometer for use in analyzing post consumer or post industrial waste carpet or Polyamide-6 and/or Polyamide-66 containing non-carpet waste, comprising:
    an infrared radiation source for irradiating infrared radiation toward a sample of waste (carpet);
    a radiation selector which selects a plurality of discrete wavelengths, said radiation selector comprising a dispersing device which disperses the radiation and a discrete wavelength selector which selects the discrete wavelengths from the dispersed radiation; and
    a detection system which detects the discrete wavelengths.

5. A hand-held infrared spectrometer according to claim 4, wherein the radiation is dispersed and select wavelengths are selected before the radiation impinges on the sample of waste (carpet).

6. A hand-held infrared spectrometer according to claim 4, wherein the radiation is dispersed and select wavelengths are selected after the radiation impinges on the sample of waste (carpet).

7. A hand-held infrared spectrometer for use in analyzing post consumer or post industrial waste carpet or Polyamide-6 and/or Polyamide-66 containing non-carpet waste, comprising:
    an infrared radiation source for irradiating infrared radiation on a sample of waste (carpet);
    a radiation selector which selects a plurality of discrete wavelengths from radiation reflected by the sample of waste (carpet), said radiation selector comprising a dispersing device which disperses the reflected radiation and a discrete wavelength selector which selects the discrete wavelengths from the dispersed radiation; and
    a detection system which detects the discrete wavelengths.

8. A hand-held infrared spectrometer according to claim 7, wherein said discrete wavelength selector comprises a plate provided with openings in locations corresponding with positions of selected discrete wavelengths in the dispersed radiation, said plate being opaque to IR radiation and being placed between the source and the detection system so that radiation cannot reach the detection system except through said openings in said plate.

9. A hand-held infrared spectrometer according to claim 8, wherein said detection system comprises plural detectors, one of each of said detectors being provided behind a respective opening in said plate.

10. A hand-held infrared spectrometer according to claim 8, wherein said detection system comprises a detector which can be disposed behind more than on of said openings in said plate.

11. A hand-held infrared spectrometer according to claim 8, further comprising a light conductor system, said light conductor system having a plurality of light conductors, each said light conductor connected to one of said openings in said plate to convey light passing through said opening in said plate to said detection system.

12. A hand-held infrared spectrometer according to claim 11, wherein said detection system comprises plural detectors and each said light conductor is connected to one of said detectors.

13. A hand-held infrared spectrometer according to claim 11, wherein the detection system and the light conductors are moveable relative to each other so that said light conductors can individually convey light to said detection system.

14. A hand-held infrared spectrometer for use in analyzing post consumer or post-industrial waste carpet or Polyamide-6 and/or Polyamide-66 containing non-carpet waste, comprising:
    an infrared radiation source for irradiating infrared radiation on a sample waste (carpet);
    a filter system comprising a plurality of filters for transmitting only predetermined wavelengths of radiation reflected with a collection angle of less than 5°; and
    a detection system which detects radiation transmitted by the filter system.

15. A hand-held infrared spectrometer according to claim 14, wherein said infrared radiation source irradiates infrared radiation on a sample of waste (carpet) and said filter system transmits only predetermined wavelengths of radiation reflected by the sample of waste (carpet).

16. A hand-held infrared spectrometer according to claim 14, wherein said filter system transmits only predetermined wavelengths of radiation to be reflected by the sample of waste (carpet).

17. A hand-held infrared spectrometer according to claim 14, wherein said filter system employs a rotary filter wheel having three or more filters.

18. A hand-held infrared spectrometer according to claim 14, wherein said filter system employs a rotary filter wheel having four filters which pass light having wavelengths of 2382 nm±20 nm, 2430 nm±20 nm, 2452 nm±20 nm, and 2472 nm±20 nm respectively.

19. A hand-held infrared spectrometer according to claim 14 wherein said filter system is an acousto optical tunable filter.

20. A method of discriminating between various types of post consumer or post industrial waste carpet or Polyamide-6 and/or Polyamide-66 containing non-carpet waste, comprising the steps of:
    providing a hand-held infrared spectrometer; and
    utilizing said hand-held infrared spectrometer to ascertain the type of material of the waste (carpet).

21. A method of discriminating between various types of post consumer of post industrial waste carpet or Polyamide-6 and/or Polyamide-66 containing non-carpet waste, comprising the steps of:

Polyamide-6 and/or Polyamide-66 containing non-carpet waste, comprising the steps of:
providing a hand-held infrared spectrometer;
irradiating infrared radiation onto a sample (carpet) waste from an infrared radiation source in said hand-held infrared spectrometer;
selecting a plurality of discrete wavelengths from radiation reflected by the sample of waste (carpet) by utilizing a radiation selector in said hand-held infrared spectrometer, said step of selecting a plurality of discrete wavelengths comprising the substep of dispersing the reflected radiation utilizing a dispersing device and the substep of selecting a plurality of discrete wavelengths from the dispersed radiation; and
detecting the discrete wavelengths with a detector provided in the hand-held infrared spectrometer, thereby utilizing said hand-held infrared spectrometer to ascertain the type of material of the waste (carpet).

22. A method of discriminating between various types of post consumer or post industrial waste carpet or Polyamide-6 and/or Polyamide-66 containing non-carpet waste, comprising the steps of:

providing a hand-held infrared spectrometer;
irradiating infrared radiation having a plurality of predetermined wavelengths onto a sample of waste (carpet) from an infrared radiation source in said hand-held infrared spectrometer, said plurality of predetermined wavelengths being selected by dispersing a beam of infrared radiation utilizing a dispersing device and selecting a plurality of discrete wavelengths from the dispersed radiation; and
detecting the discrete wavelengths with a detector provided in the hand-held infrared spectrometer, thereby utilizing said hand-held infrared spectrometer to ascertain the type of material of the waste (carpet).

23. A method of discriminating between various types of post consumer or post industrial waste carpet or Polyamide-6 and/or Polyamide-66 containing non-carpet waste, comprising the steps of:

providing a hand-held infrared spectrometer;
irradiating infrared radiation onto a sample of waste from an infrared radiation source in said hand-held infrared spectrometer;
selecting a plurality of discrete wavelengths from radiation reflected by the sample of waste (carpet) by utilizing a radiation selector in said hand-held infrared spectrometer, said step of selecting a plurality of discrete wavelengths comprising the substep of filtering the reflected radiation to thereby allow radiation of a plurality of predetermined wavelengths to pass to a detector system provided in the hand-held infrared spectrometer; and
detecting the discrete wavelengths with the detector provided in the hand-held infrared spectrometer, thereby utilizing said hand-held infrared spectrometer to ascertain the type of material of the waste (carpet).

24. A method of discriminating between various types of post consumer or post industrial waste carpet or Polyamide-6 and/or Polyamide-66 containing non-carpet waste, comprising the steps of:

providing a hand-held infrared spectrometer; irradiating infrared radiation having a plurality of predetermined wavelengths onto a sample of waste (carpet) from an infrared radiation source in said hand-held infrared spectrometer, said plurality of predetermined wavelengths being selected by filtering a beam of infrared radiation utilizing a plurality of filters; and
detecting the discrete wavelengths with the detector provided in the hand-held infrared spectrometer, thereby utilizing said hand-held infrared spectrometer to ascertain the type of material of the waste (carpet).

* * * * *